(12) United States Patent
Bäckström et al.

(10) Patent No.: US 11,534,446 B2
(45) Date of Patent: *Dec. 27, 2022

(54) PHARMACEUTICAL COMPOSITION COMPRISING 3-BETA-HYDROXY-5-ALPHA-PREGNAN-20-ONE WITH IMPROVED STORAGE AND SOLUBILITY PROPERTIES

(71) Applicant: ASARINA PHARMA AB, Solna (SE)

(72) Inventors: Torbjörn Bäckström, Umeå (SE); Anders Carlsson, Stockholm (SE)

(73) Assignee: ASARINA PHARMA AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/601,214

(22) Filed: May 22, 2017

(65) Prior Publication Data

US 2017/0258809 A1 Sep. 14, 2017

Related U.S. Application Data

(60) Continuation of application No. 14/626,490, filed on Feb. 19, 2015, now Pat. No. 9,687,496, which is a (Continued)

(30) Foreign Application Priority Data

Jan. 14, 2010 (SE) .................... 1050029-6

(51) Int. Cl.
*A61K 31/57* (2006.01)
*A61K 31/575* (2006.01)
(Continued)

(52) U.S. Cl.
CPC ............ *A61K 31/57* (2013.01); *A61K 9/10* (2013.01); *A61K 9/107* (2013.01); *A61K 31/575* (2013.01);
(Continued)

(58) Field of Classification Search
CPC ...... A61K 31/57; A61K 31/575; A61K 47/14; A61K 47/28; A61K 47/44; A61K 9/0019
See application file for complete search history.

(56) References Cited

U.S. PATENT DOCUMENTS 5,120,723 A 6/1992 Gee et al.
5,364,632 A 11/1994 Benita et al.
(Continued)

FOREIGN PATENT DOCUMENTS

EP 1063999 B1 10/2005
JP 54-122719 A 9/1979
(Continued)

OTHER PUBLICATIONS

Park et al (Korean Journal of Fisheries and Aquatic Sciences, 1981; 14(1):1-6) (abstract) (Year: 1981).*
(Continued)

*Primary Examiner* — Marcos L Sznaidman
*Assistant Examiner* — Rayna Rodriguez
(74) *Attorney, Agent, or Firm* — Cermak Nakajima & McGowan LLP; Malcolm K. McGowan (57) ABSTRACT

It is provided a pharmaceutical composition comprising 3-beta-hydroxy-5-alpha-pregnan-20-one, at least one sterol or an ester thereof and a mixture of acylglycerols with a solid fat content of less than 25% at 25° C. and 0% at 37° C. In addition it is provided a method for preparing the pharmaceutical composition.

19 Claims, 3 Drawing Sheets

Mean plasma concentrations of 3-beta-hydroxy-5-alpha-pregnan-20-one (ng/mL)

Related U.S. Application Data division of application No. 13/522,081, filed as application No. PCT/SE2011/050036 on Jan. 14, 2011, now abandoned.

(60) Provisional application No. 61/295,027, filed on Jan. 14, 2010.

(51) Int. Cl.

| | | |
|---|---|---|
| *A61K 9/10* | (2006.01) | |
| *A61K 9/107* | (2006.01) | |
| *A61K 47/14* | (2017.01) | |
| *A61K 47/28* | (2006.01) | |
| *A61K 47/44* | (2017.01) | |
| *A61K 9/00* | (2006.01) | |

(52) U.S. Cl.
CPC .............. *A61K 47/14* (2013.01); *A61K 47/28* (2013.01); *A61K 47/44* (2013.01); *A61K 9/0019* (2013.01); *A61K 9/0034* (2013.01); *A61K 9/0043* (2013.01)

(56) References Cited

U.S. PATENT DOCUMENTS

| | | | |
|---|---|---|---|
| 5,449,474 | A | 9/1995 | Lucas et al. |
| 5,643,604 | A * | 7/1997 | Angeles Uribe .... A61K 9/1617 424/489 |
| 5,645,856 | A | 7/1997 | Lacy et al. |
| 5,763,431 | A | 6/1998 | Jackson |
| 6,075,058 | A | 6/2000 | Handelman |
| 6,096,338 | A | 8/2000 | Lacy et al. |
| 6,455,516 | B1 | 9/2002 | Backstrom et al. |
| 6,855,721 | B1 | 2/2005 | Murphy et al. |
| 6,888,721 | B1 | 5/2005 | Moghaddam et al. |
| 2003/0236236 | A1 | 12/2003 | Chen et al. |
| 2004/0204490 | A1 | 10/2004 | Farb et al. |
| 2005/0096296 | A1 | 5/2005 | Fikstad et al. |
| 2005/0096365 | A1 | 5/2005 | Fikstad et al. |
| 2005/0222099 | A1 | 10/2005 | Backstrom et al. |
| 2005/0256029 | A1 | 11/2005 | Murphy et al. |
| 2006/0003002 | A1 | 1/2006 | Fikstad et al. |
| 2008/0070876 | A1 | 3/2008 | Backstrom et al. |
| 2008/0119416 | A1 | 5/2008 | Backstrom et al. |
| 2008/0269183 | A1 | 10/2008 | Mellon et al. |
| 2010/0136105 | A1 | 6/2010 | Chen et al. |
| 2010/0137271 | A1* | 6/2010 | Chen .................. A61B 17/0485 514/181 |

FOREIGN PATENT DOCUMENTS

| | | |
|---|---|---|
| JP | 2-286625 A | 11/1990 |
| WO | WO 93/03732 A1 | 3/1993 |
| WO | WO 95/01162 A1 | 1/1995 |
| WO | WO 95/05826 A1 | 3/1995 |
| WO | WO 96/16076 A1 | 5/1996 |
| WO | WO 98/50042 A1 | 11/1998 |
| WO | WO 99/45931 A1 | 9/1999 |
| WO | WO 00/59945 A1 | 10/2000 |
| WO | WO 01/08670 A2 | 2/2001 |
| WO | WO 01/16601 A1 | 3/2001 |
| WO | WO 03/059357 A1 | 7/2003 |
| WO | WO 2006/037016 A2 | 4/2006 |
| WO | WO 2006/054938 A1 | 5/2006 |
| WO | WO 2008/063128 A1 | 5/2008 |

OTHER PUBLICATIONS

Abitec, "Capmul® MCM EP," Technical Data Sheet, Feb. 10, 2014, 1 page, http://www.abiteccorp.com/wp-content/files_mf/1392129289CapmulMCMEPTDSI10.pdf (obtained from the internet Jun. 11, 2015).

Alander et al. (Lidefelt, Editor), "Handbook: Vegetabie Oils and Fats," AarhusKarlshamn, 2007, pp. 1-253 (255 pages total).

Bäckström et al., "Isoallopregnanolone; an antagonist to the anaesthetic effect of allopregnanolone in male rats," European Journal of Pharmacology, vol. 512, Issue 1, Apr. 4, 2005 (available online Mar. 17, 2005), pp. 15-21.

Blaha et al., "Deciduomal Responses in the Uteri of Ovariectomized Golden Hamsters, Comparing Progesterone and Three Closely Related Steroids Applied in Utero," Biology of Reproduction, vol. 18, 1978, pp. 441-447.

Caelo, "Miglyol® 812," Material Safety Data Sheet, INCI-Name, Feb. 18, 2015, pp. 1-3 (see p. 1) (obtained from the internet www.caelo.de/getfile.html?type=sdb_en&cntry=en&num=3274, Jun. 11, 2015).

Champion et al., "Role of Particle Size in Phagocytosis of Polymeric Microspheres," Pharm. Res., vol. 25, No. 8, Aug. 2008, pp. 1815-1821.

Do-Rego et al., "γ-Aminobutyric acid, acting through γ-aminobutyric acid type A receptors, inhibits the biosynthesis of neurosteroids in the frog hypothalamus," PNAS, vol. 97, No. 25, Dec. 5, 2000, pp. 13925-13930.

Gonzalez-Mariscal et al., "Anesthetic Pregnanes Counteract Androgen-Induced Defeminization," Neuroendocrinology, vol. 34, No. 5, 1982, pp. 357-362 (Abstract; p. 358, left column, lines 9-10 from bottom).

Grant et al., "Neuroactive Steroid Stereospecificity of Ethanol-Like Discriminative Stimulus Effects in Monkeys," The Journal of Pharmacology and Experimental Therapeutics, vol. 326, No. 1, Jul. 2008, pp. 354-361.

Gunstone et al., "Lipid Glossary 2," The Oily Press, 2000, pp. 1-237 (246 pages total).

Hedström et al., "Studies of pharmacokinetic and pharmacodynamics properties of isoailopregnanolone in healthy women," Psychopharmacology, vol. 203, 2009 (Published online Oct. 24, 2008), pp. 85-89.

Hogenkamp et al., "Synthesis and in Vitro Activity of 3β-Substituted-3α-hydroxypregnan-20-ones: Allosteric Modulators of the GABAA Receptor," J. Med. Chem., vol. 40, No. 1, 1997 (Published on the Web Jan. 3, 1997), pp. 61-72.

International Preliminary Report on Patentability and Written Opinion of the International Searching Authority (PCT/IB/326, PCT/IB/373 and PCT/ISA/237) for International Application No. PCT/SE2011/050036, dated Jul. 26, 2012.

International Search Report (PCT/ISA/210) for International Application No. PCT/SE2011/050036, dated Mar. 3, 2011.

Mackenzie et al., "The Role of Neuroactive Steroids in Anxiety Disorders," Chapter 21, Neuroactive Steroids in Brain Function, Behavior and Neuropsychiatric Disorders, Springer 2008, pp. 435-447.

Strickley, "Solubilizing Excipients in Oral and Injectable Formulations," Pharmaceutical Research, vol. 21, No. 2, Feb. 2004, pp. 201-230.

Wang et al., "Analysis of neurosterols and neurosteroids by mass spectrometry," Biochimie, vol. 89, 2007 (Available online Nov. 2, 2006), pp. 182-191.

Wang et al., "The inhibitory effects of allopregnanolone and pregnanolone on the population spike, evoked in the rat hippocampal CA1 stratum pyramidale in vitro, can be blocked selectively by epiallopregnanolone," Acta Physiol Scand., vol. 169, 2000, pp. 333-341.

Blaha, G. C., et al., "Deciduomal Responses in the Uteri of Ovariectomized Golden Hamsters, Comparing Progesterone and Three Closely Related Steroids Applied in utero," Biol. Reproduction 1978;18(3):441-447.

Strickley, R. G., "Solubilizing Excipients in Oral and Injectable Formulations," Pharm. Res. 2004;21(2):201-230.

\* cited by examiner

PHARMACEUTICAL COMPOSITION COMPRISING 3-BETA-HYDROXY-5-ALPHA-PREGNAN-20-ONE WITH IMPROVED STORAGE AND SOLUBILITY PROPERTIES

CROSS REFERENCE TO RELATED APPLICATIONS

This application is a Continuation of copending application Ser. No. 14/626,490, filed on Feb. 19, 2015, which is a Divisional of application Ser. No. 13/522,081, filed on Aug. 17, 2012, which was filed as PCT International Application No. PCT/SE2011/050036 on Jan. 14, 2011, which claims the benefit under 35 U.S.C. § 119(e) to U.S. Provisional Application No. 61/295,027, filed on Jan. 14, 2010, and under 35 U.S.C. § 119(a) to Patent Application No. 1050029-6, filed in SWEDEN on Jan. 14, 2010, all of which are hereby expressly incorporated by reference into the present application.

TECHNICAL FIELD

The present invention relates generally to an improved formulation of 3-beta-hydroxy-5-alpha-pregnan-20-one.

BACKGROUND ART 3-beta-hydroxy-5-alpha-pregnan-20-one is a steroid in the pregnane family and a modulator of $GABA_A$-receptor activity which is indicated for the treatment of sex/stress steroid induced disorders conditions (WO99/45931). 3-beta-hydroxy-5-alpha-pregnan-20-one is poorly soluble in many therapeutically acceptable solvents, which makes it difficult to administer the compound to a patient.

In animal studies, 3-beta-hydroxy-5-alpha-pregnan-20-one has been intravenously administered to rats in a formulation containing cyclodextrin (WO99/45931).

Grant et al (JPET 326:354-362, 2008) has administered 3-beta-hydroxy-5-alpha-pregnan-20-one to monkeys by using a formulation with hydroxypropyl β-cyclodextrin.

Formulations with cyclodextrins are not suitable for administration to human patients. One reason for this is, because 3-beta-hydroxy-5-alpha-pregnan-20-one is poorly soluble, the formulation results in a large therapeutic volume that can only be administered intravenously.

Since 3-beta-hydroxy-5-alpha-pregnan-20-one is poorly soluble in water there is still no pharmaceutically acceptable formulation for this compound.

Definitions

As used in the present application, the following terms have the specified meanings unless otherwise specified.

By "acylglycerol" is meant all types and combinations of fatty acids esterified to glycerol.

By "medium-chain acylglycerol" is meant a mixture of acylglycerols where the total combined percentage of octanoic (caprylic) acid and decanoic (capric) acid is at least 95%.

By "solid fat content" is meant the percentage of solid as determined by pulse NMR (nuclear magnetic resonance).

"Room temperature" denotes a temperature of between 18° C. and 25° C.

"UC1010" denotes 3-beta-hydroxy-5-alpha-pregnan-20-one.

"Sterol or ester thereof" denotes steroids with at least one hydroxyl group and esters of said steroids where at least one hydroxyl group has been used for the synthesis of an ester.

Steroids, such as sterols, are usually described by the number of carbon atoms in the compound. Thus, for example, cholesterol is a C27 sterol, which indicates that the compound consists of 27 carbon atoms.

Unless stated otherwise, concentrations are stated as mg/g, that is, mg per gram of pharmaceutical composition.

SUMMARY OF INVENTION

An object of the present invention is to provide an improved formulation of 3-beta-hydroxy-5-alpha-pregnan-20-one in a pharmaceutically acceptable carrier.

Another object of the present invention is to provide a formulation of 3-beta-hydroxy-5-alpha-pregnan-20-one with enhanced storage properties.

Yet another object is to provide a formulation of 3-beta-hydroxy-5-alpha-pregnan-20-one with improved pharmacokinetics.

Yet another object of the present invention is to provide a formulation of 3-beta-hydroxy-5-alpha-pregnan-20-one with increased solubility in a pharmacologically acceptable carrier.

These and other objects are met by a first general aspect of the present invention which provides a pharmaceutical formulation comprising 3-beta-hydroxy-5-alpha-pregnan-20-one, at least one sterol or an ester thereof and a mixture of acylglycerols with a solid fat content of less than about 25% at 25° C. and about 0% at 37° C.

In a second general aspect of the present invention there is provided methods for preparing a pharmaceutical composition.

In a third general aspect of the present invention there is provided a pharmaceutical composition obtainable according to a method according to the invention.

In a fourth general aspect of the present invention there is provided use of a pharmaceutical composition for the treatment of conditions of the central nervous system.

DETAILED DESCRIPTION

The inventors have found that the addition of a sterol surprisingly increases the solubility and improves the pharmacokinetics of 3-beta-hydroxy-5-alpha-pregnan-20-one in acylglycerols.

Generally, the pharmaceutical composition comprises 3-beta-hydroxy-5-alpha-pregnan-20-one, at least one sterol or an ester thereof and a mixture of acylglycerols with a solid fat content of less than about 25% at 25° C. and about 0% at 37° C.

In particular a sterol with a hydroxyl group bound to the third carbon atom of the sterol structure is useful in the invention. The sterol may be cholesterol or beta-sitosterol, but also other sterols such as stigmasterol, brassicasterol or avenasterol may be used. In particular, cholesterol may be used.

In addition, cholesteryl esters can be used. Examples of such esters are sodium cholesteryl sulphate, cholesteryl bensoate, cholesteryl acetate, cholesteryl caprylate, cholesteryl decanoate, cholstyl palmitate, cholesteryl oleate and cholesteryl stearate.

The sterol or ester thereof can be a C18-C30 sterol or an ester thereof, a C21-C27 sterol or an ester thereof, or a C27-C29 sterol or ester thereof.

The pharmaceutical composition can, in a first embodiment, be such that 3-beta-hydroxy-5-alpha-pregnan-20-one is essentially dissolved in the composition. Thus 3-beta-hydroxy-5-alpha-pregnan-20-one can be dissolved or essentially dissolved according to this embodiment of the invention.

The weight ratio of sterol (or ester thereof) to 3-beta-hydroxy-5-alpha-pregnan-20-one can, in this embodiment, be in the range of about 1:10 to 10:1. The sterol or ester thereof may be added in an amount that is similar to the amount of 3-beta-hydroxy-5-alpha-pregnan-20-one by weight. Because 3-beta-hydroxy-5-alpha-pregnan-20-one and a sterol have similar molecular weights this results in almost equimolar amounts of 3-beta-hydroxy-5-alpha-pregnan-20-one to sterol.

Thus, the weight ratio of sterol to 3-beta-hydroxy-5-alpha-pregnan-20-one can be in the range of from 1:5 to 5:1. In particular, the weight ratio of sterol to 3-beta-hydroxy-5-alpha pregnan-20-one can be from 1:3 to 3:1.

Suitable concentrations of 3-beta-hydroxy-5-alpha pregnan-20-one are between 0.1 mg/g and 75 mg/g. The concentration of 3-beta-hydroxy-5-alpha pregnan-20-one can also be between 1 mg/g and 50 mg/g, between 5 mg/g and 30 mg/g or between 10 mg/g and 25 mg/g.

Alternatively, in a second embodiment, the pharmaceutical composition comprises a suspension of 3-beta-hydroxy-5-alpha-pregnan-20-one. In this case the pharmaceutical composition will comprise 3-beta-hydroxy-5-alpha-pregnan-20-one in particles as well as 3-beta-hydroxy-5-alpha-pregnan-20-one dissolved in the composition. The sterol increases the soluble fraction of 3-beta-hydroxy-5-alpha-pregnan-20-one in such a suspension compared to a suspension without a sterol. One advantage with a suspension is that the formulation can contain a high concentration of 3-beta-hydroxy-5-alpha-pregnan-20-one. An additional advantage with a composition that comprises a suspension is that it results in slow release of 3-beta-hydroxy-5-alpha-pregnan-20-one.

When the pharmaceutical composition comprises a suspension, the particles are preferably of a range of sizes that is not engulfed by macrophages. Macrophages do primarily engulf particles of a size that is 2-3 micrometer (Champion et al, Pharm Res 2008; 25(8):1815-1821).

In this second embodiment, the weight ratio of sterol (or ester thereof) to 3-beta-hydroxy-5-alpha pregnan-20-one can be in the range of about 1:10 to 10:1. The weight ratio of sterol to 3-beta-hydroxy-5alpha pregnan-20-one can be in the range of from 1:5 to 5:1. In particular, the weight ratio of sterol to 3-beta-hydroxy-5-alpha-pregnan-20-one can be from 1:4 to 3:1 or from 1:3 to 3:1.

Suitable concentrations of 3-beta-hydroxy-5-alpha-pregnan-20-one are, in this second embodiment, between 0.1 mg/g and 750 mg/g. The concentration of 3-beta-hydroxy-5-alpha-pregnan-20-one can also be between 1 mg/g and 300 mg/g, between 1 mg/g and 100 mg/g, between 1 mg/g and 50 mg/g, between 5 mg/g and 30 mg/g or between 10 mg/g and 25 mg/g.

The following applies to the invention in general.

Generally, the mixture of acylglycerols is characterized in that it has a solid fat content of less than about 25% at 25° C. and about 0% at 37° C. Thus, the solid fat content is, for practical purposes, 0% at 37° C. The solid fat content is at most 0.01% at 37° C.

The mixture of acylglycerols can be a vegetable oil. Thus, it can be a vegetable oil selected from the group consisting of sesame oil, peanut oil, olive oil, and castor oil, or mixtures thereof.

In particular the mixture of acylglycerols can be a medium-chain acylglycerol, that is, a mixture of acylglycerols wherein the total combined percentage of fatty acids with 8 carbon atoms (octanoic acid) and 10 carbon atoms (decanoic acid) is at least 95%. The medium-chain acylglycerol can be various mixtures of monoacylglycerols, diacylglycerols and triacylglycerols.

The medium-chain acylglycerol can consist of from about 50% to about 65% of monoacylglycerols, about 25% to about 35% of diacylglycerols, less than about 5% of triacylglycerols and less than about 2.5% of glycerol. An example of such a medium chain acylglycerol is Akoline MCM.

The medium-chain acylglycerol can be such that it comprises at least about 95% triacylglycerols. Akomed R MCT is an example of such a medium-chain acylglycerol.

The mixture of acylglycerols can comprise a mixture of a vegetable oil and a medium-chain acylglycerol. The mixture of acylglycerols can comprises a mixture of castor oil and a medium-chain acylglycerol where castor oil is present in an amount of between 40% and 60% by weight. The mixture of acylglycerols can consist of about 48% by weight of castor oil and about 52% by weight of a medium-chain acylglycerol. In particular the mixture of acylglycerols can consist of about 48% by weight castor oil and about 52% by weight of a medium-chain acylglycerol.

The pharmaceutical composition may comprise additional excipients known to a person skilled in the art such as antioxidants, preservatives, surfactants, coloring, flavoring, or thickening agents.

The pharmaceutical composition can be administered to the patient by different means. Thus, it may be administered orally, parenterally or topically. Thus, the pharmacological composition may be administered subcutaneously, intramuscularly, intravenously, nasally, transdermally or vaginally.

In a second general aspect of the present invention there is provided methods for preparing a pharmaceutical composition of 3-beta-hydroxy-5-alpha-pregnan-20-one.

One method, in which 3-beta-hydroxy-5-alpha-pregnan-20-one is dissolved or essentially dissolved in the composition, comprises the steps of a) dissolving 3-beta-hydroxy-5-alpha-pregnan-20-one in ethanol, b) adding a mixture of acylglycerols with a solid fat content of less than about 25% at 25° C. and about 0% at 37° C. and a sterol or ester thereof, c) mixing until a homogeneous liquid is obtained and d) evaporating the ethanol.

When the mixture of acylglycerol is a solid or a semi-solid at room temperature, such as a medium-chain acylglycerol, the method may comprise a further step, which is the melting of the medium-chain acylglycerol before mixing it with the ethanol-drug preparation. The melting step enables the homogeneous mixing of this type of acylglycerol with other components. Once melted and mixed with the other components, the preparation remains in a liquid state for at least the time periods indicated in Table 1.

When the formulation comprises a suspension, the formulation is advantageously prepared according to a method that comprises the following steps: 1) dissolving or suspending the sterol or ester thereof in the mixture of acylglycerols, 2) suspending 3-beta-hydroxy-5-alpha-pregnan-20-one in the acylglycerol-sterol mixture, 3) gently mixing. Surprisingly, this procedure leads to suspended particles comprising 3-beta-hydroxy-5-alpha-pregnan-20-one of smaller size.

In a third general aspect of the present invention there is provided pharmaceutical compositions obtainable by the methods according to the second aspect of the invention.

In a fourth general aspect of the present invention there is provided the use of the pharmaceutical composition according to the invention for the treatment or prevention of conditions of the central nervous system.

The pharmaceutical composition can be used to treat or prevent conditions of the central nervous system. Examples of such conditions that can be treated are epilepsy, menstruation cycle dependant epilepsy, depression, stress related depression, migraine, tiredness and in particular stress related tiredness, premenstrual syndrome, premenstrual dysphoric disorder, menstrual cycle linked mood changes, stress related memory changes, menstrual cycle linked memory changes, Alzheimer's dementia, menstrual cycle linked difficulties in concentration, menstrual cycle linked sleep disorders and tiredness, substance abuse, menstrual cycle linked alcoholism, or combinations thereof.

In particular the pharmaceutical composition can be used to treat steroid induced mood disorders, in particular premenstrual dysphoric disorder.

The pharmaceutical composition can also be used for treating or preventing side effects of oral contraceptives and postmenopausal therapy.

The pharmaceutical composition can also be used for control or termination of steroid-induced anesthesia.

EXAMPLES

The invention will now be described with non-limiting examples.

In order to find a pharmaceutical composition comprising 3-beta-hydroxy-5-alpha-pregnan-20-one, several different vehicles and combinations of vehicles were evaluated. 3-beta-hydroxy-5-alpha-pregnan-20-one was dissolved in various vehicles and was evaluated by eye for physical stability at room temperature over time. A formulation that did not undergo any visible changes in appearance and remained clear on storage in room temperature without signs of haziness, precipitation, sedimentation, phase separation into two or more liquid phases or change of colour, within 30 days was considered as "stable".

In addition, the particle size and solubility of 3-beta-hydroxy-5-alpha-pregnan-20-one in formulations comprising a suspension of 3-beta-hydroxy-5-alpha-pregnan-20-one were evaluated.

General Procedure for Examples 1-49

The following procedure was adopted for the preparation of 3-beta-hydroxy-5-alpha-pregnan-20-one-containing formulations.

The desired amount of 3-beta-hydroxy-5-alpha-pregnan-20-one and sterol (for example cholesterol) was weighed in a 100 ml or 250 ml round-bottomed flask. To every gram of the mixture of 3-beta-hydroxy-5-alpha-pregnan-20-one and sterol a volume of about 30 ml of absolute ethanol was added. The mixture was treated in an ultrasonication bath (not exceeding 50° C.) until a clear liquid was obtained. This was normally accomplished within 10 minutes. The additional lipid ingredients indicated in the "Vehicle" column in Table 1 was then added up to 20 g. The resulting mixture was gently shaken by hand until a clear, homogeneous liquid was obtained. When the lipid was a solid at room temperature it was melted in the warm ultrasonication bath to a liquid form before addition.

Compounds from the following suppliers were used (product numbers within brackets): Cholesterol from Sigma (C8503), olive oil and peanut oil from Apoteket, Sweden (26 36 16 and 26 66 01, respectively), sesame oil from Fluka (85067), and castor oil from Sigma (259853). Akomed R medium-chain triacylglycerol (MCT) and Akoline medium-chain monoacylglycerol (MCM) were both from AarhusKarlshamns Sweden AB, Karlshamn, Sweden.

The alcohol was evaporated from the liquid on a rotary evaporator at a pressure of about 25 mbar and a temperature of about 40° C. until the weight of the flask was essentially constant. The remaining ethanol content was essentially less than 1%. The aim was to obtain a liquid with the appearance of clear oil at room temperature. The oily liquid was then transferred to clear glass vials and stored at room temperature until evaluation.

The samples were evaluated by observing the samples in the glass vials and recording signs of haziness, precipitation, sedimentation, phase separation into two or more liquid phases, or change of colour after 1 or 2 days after preparation and after 30 days after preparation. In some cases, other time intervals were used (indicated in Table 1). Where indicated, the entire sample was placed in a refrigerator (2-8° C.) to provoke precipitation.

Example 1

3-beta-hydroxy-5-alpha-pregnan-20-one (UC1010) (5 mg/g) and peanut oil was mixed into an emulsion with ethanol as described above in the concentrations shown in Table 1, and the ethanol was evaporated. The final weight of the preparation was 20 g. The mixture then had the form of an oily liquid. After one day when the sample was evaluated there were signs of precipitation. At 30 days the precipitate has formed a bottom sediment. Thus, the formulation was not stable.

Example 2

Example 2 was carried out essentially as Example 1 with the difference that cholesterol (5.5 mg/g) was added. When the sample was evaluated after one day the appearance of the sample had not changed. It was still unchanged after 30 days and after four months. After five months there was a slight precipitation. Example 2 compared with Example 1 shows how the addition of 5.5 mg/g cholesterol to a solution of 5 mg/g 3-beta-hydroxy-5-alpha-pregnan-20-one in peanut oil substantially increases the solubility so that, instead of precipitating, no precipitation occurred and the sample was stable for four months. However, a slight sedimentation occurred after 5 months.

Examples 3 to 49

Examples 3 to 49 were carried out essentially as described above with the variations with regard to 3-beta-hydroxy-5-alpha-pregnan-20-one concentration, acylglycerol mixture used, sterol used and sterol concentration that are shown in Table 1.

The data from examples 1 to 49 is presented in Table 1. The effect of addition of cholesterol is, for example, evident in examples 8 and 12, where the addition of cholesterol (10 mg/g) substantially increased solubility so that the sample did not precipitate but instead was stable for 12 months.

In Table 1, "Weighed amount of UC1010 (mg/g)" is the amount of 3-beta-hydroxy-5-alpha-pregnan-20-one per gram of final total composition including sterol (when a sterol is present). "Vehicle" denotes the carrier being tested. The amount of sterol is stated as "mg/g", that is, the weight of sterol per weight of final total composition, including 3-beta-hydroxy-5-alpha-pregnan-20-one. "Appearance at preparation" describes the change of appearance of the mixture during preparation; usually the preparation is initially an emulsion or a solution whereas it has an oily appearance after evaporation of the ethanol; "Unchanged" denotes a sample that was stable and where thus 3-beta-hydroxy-5-alpha-pregnan-20-one remained in solution, without visible signs of haziness, precipitation, sedimentation, phase separation into two or more liquid phases or change of colour. This is also indicated by an asterisk (*) in the table.

TABLE 1

| Example | Batch name | Weighed amount of UC1010 (mg/g) | Vehicle | Appearance at preparation | Appearance after 1-2 days or other time period that is indicated | Appearance after 30 days or other time period that is indicated | Comments |
|---|---|---|---|---|---|---|---|
| 1 | ACA09 0630-1 | 5 | Peanut oil | Emulsion to oil | Signs of precipitation | Bottom sediment | |
| 2 | ACA09 0629-6 | 5 | Peanut oil + cholesterol (5.5 mg/g) | Emulsion to oil | Unchanged * | Slight sedimentation after 5 months | |
| 3 | ACA09 0629-4 | 10 | Peanut oil | Emulsion to suspension | Precipitation in almost the entire sample volume | | |
| 4 | ACA09 0629-3 | 10 | Peanut oil + cholesterol (10 mg/g) | Emulsion to oil (precipitation after a few hours) | Bottom sediment | | |
| 5 | ACA09 0629-5 | 20 | Peanut oil + cholesterol (20 mg/g) | Emulsion to oil (precipitation after a few hours) | Bottom sediment | | |
| 6 | ACA09 0629-8 | 10 | Olive oil + cholesterol (10 mg/g) | Emulsion to oil | Bottom sediment | | |
| 7 | ACA09 0709-2 | 3 | Sesame oil + cholesterol (3 mg/g) | Emulsion to oil | Unchanged * | Slight sedimentation after 13 months | |
| 8 | ACA09 0702-2 | 5 | Sesame oil | Emulsion to oil | Precipitation | Bottom sediment | |
| 9 | ACA09 0822-B | 5 | Sesame oil + cholesterol (2.5 mg/g) | Emulsion to oil | Unchanged * | Precipitation of crystals after 2 months | |
| 10 | ACA09 0702-1 | 5 | Sesame oil + cholesterol (5 mg/g) | Emulsion to oil | Unchanged * | A few particles on the bottom | |
| 11 | ACA09 0822-A | 5 | Sesame oil + cholesterol (5 mg/g) | Emulsion to oil | Unchanged * | Precipitation of crystals after 2 months | |
| 12 | ACA09 0822-C | 5 | Sesame oil + cholesterol (10 mg/g) | Emulsion to oil | Unchanged * | Unchanged after 12 months * | |
| 13 | ACA09 0822-E | 10 | Sesame oil + cholesterol (5 mg/g) | Emulsion to oil | Precipitation of crystals | | |
| 14 | ACA09 0822-D | 10 | Sesame oil + cholesterol (10 mg/g) | Emulsion to oil | Precipitation of crystals | | |
| 15 | ACA09 0822-F | 11 | Sesame oil + cholesterol (20 mg/g) | Emulsion to oil | Precipitation of crystals | | |
| 16 | ACA09 0716-7 | 10 | Sesame oil + β-sitosterol (10 mg/g) | Emulsion to oil | Unchanged * | Crystals on the bottom an on the walls of the vial | |
| 17 | ACA09 1024-1 | 10 | Akomed R MCT | Solution to oil | Precipitation of crystals within an hour | | |
| 18 | ACA09 1024-2 | 10 | Akomed R MCT + cholesterol (10 mg/g) | Solution to oil | Slight precipitation of crystals on the bottom after 2 days | | |
| 19 | ACA09 1025-1 | 15 | Akomed R MCT + cholesterol (15 mg/g) | Solution to oil | Slight precipitation of crystals on the bottom after 24 hours | | |
| 20 | ACA09 1024-3 | 10 | 50% Akomed R MCT, 50% Akoline MCM | Solution to oil | Unchanged * | Unchanged after 10 months * | |
| 21 | ACA09 1024-4 | 10 | 50% Akomed R MCT, 50% Akoline MCM + cholesterol (10 mg/g) | Solution to oil | Unchanged * | Unchanged after 10 months * | |

TABLE 1-continued

| Example | Batch name | Weighed amount of UC1010 (mg/g) | Vehicle | Appearance at preparation | Appearance after 1-2 days or other time period that is indicated | Appearance after 30 days or other time period that is indicated | Comments |
|---|---|---|---|---|---|---|---|
| 22 | ACA09 1025-2 | 15 | 50% Akomed R MCT, 50% Akoline MCM | Solution to oil | Slight precipitation of crystals on the bottom after 1 week | | |
| 23 | ACA09 1025-3 | 15 | 50% Akomed R MCT, 50% Akoline MCM + cholesterol (15 mg/g) | Solution to oil | Unchanged * | Unchanged after 10 months * | |
| 24 | ACA09 1026-1 | 20 | 50% Akomed R MCT, 50% Akoline MCM | Solution to oil | Slight precipitation of crystals on the bottom after 24 hours | | |
| 25 | ACA09 1026-2 | 20 | 50% Akomed R MCT, 50% Akoline MCM + cholesterol (20 mg/g) | Solution to oil | Unchanged * | Very slight precipitation after 2.5 months | |
| 26 | ACA09 1101-1 | 25 | 50% Akomed R MCT, 50% Akoline MCM + cholesterol (25 mg/g) | Solution to oil | Slight precipitation of crystals on the bottom after 3 days | | |
| 27 | ACA09 1102-1 | 30 | 50% Akomed R MCT, 50% Akoline MCM + cholesterol (30 mg/g) | Solution to oil | First sign of precipitation after 2 days | | |
| 28 | ACA09 1025-4 | 15 | Castor oil | Solution to oil | Slight precipitation of crystals on the bottom after 26 days | | |
| 29 | ACA09 1026-3 | 20 | Castor oil | Solution to oil | Slight precipitation of crystals on the bottom after 3 days | | |
| 30 | ACA09 1101-2 | 20 | Castor oil + cholesterol (20 mg/g) | Solution to oil | Unchanged * | Unchanged after 10 months * | |
| 31 | ACA09 1109-1 | 25 | Castor oil + cholesterol (25 mg/g) | Solution to oil | Unchanged * | Unchanged after 1 month, very slight precipitation after 2 months | Unchanged after 1 week refrigerated * |
| 32 | ACA09 1109-2 | 30 | Castor oil + cholesterol (31 mg/g) | Solution to oil | Slight precipitation of crystals on the bottom after 8 days | | Small crystals on the bottom after 1 week refrigerated - unchanged after 2 days * |
| 33 | ACA09 1122-1 | 40 | Akoline MCM | Solution to oil | Massive precipitation within an hour | | |
| 34 | ACA09 1122-2 | 40 | Akoline MCM + cholesterol (40 mg/g) | Solution to oil | Unchanged after 24 hours * | Precipitation after 1 week | |
| 35 | ACA09 1101-4 | 25 | 50% Castor oil, 50% Akoline MCM + cholesterol (25 mg/g) | Solution to oil | Unchanged * | Unchanged after 10 months * | After 1 week refrigerated, the entire sample was solidified, Slight precipitation after melting |
| 36 | ACA09 1102-2 | 30 | 50% Castor oil, 50% Akoline MCM + cholesterol (30 mg/g) | Solution to oil | Unchanged * | Unchanged after 1 month, very slight precipitation after approx 2 months | After 1 week refrigerated, the entire sample was solidified, Slight precipitation after melting |
| 37 | ACA09 1108-1 | 34 | 48% Castor oil, 52% Akoline MCM + cholesterol (34 mg/g) | Solution to oil | Unchanged after 15 days * | Precipitation in entire sample after 1 month | Unchanged * after 1 week refrigerated |
| 38 | ACA09 1108-2 | 38 | 50% Castor oil, 50% Akoline MCM + cholesterol (38 mg/g) | Solution to oil | Slight precipitation of crystals on the bottom after 9 days | | Small crystals on the bottom after 1 week |

TABLE 1-continued

| Example | Batch name | Weighed amount of UC1010 (mg/g) | Vehicle | Appearance at preparation | Appearance after 1-2 days or other time period that is indicated | Appearance after 30 days or other time period that is indicated | Comments |
|---|---|---|---|---|---|---|---|
| | | | | | | | refrigerated - unchanged after 2 days |
| 39 | ACA09 1120-3 | 40 | 50% Castor oil, 50% Akoline MCM + cholesterol (20 mg/g) | Solution to oil | Massive precipitation after 24 hours | | |
| 40 | ACA09 1120-1 | 40 | 50% Castor oil, 50% Akoline MCM + cholesterol (40 mg/g) | Solution to oil | Massive precipitation after 24 hours | | |
| 41 | ACA09 1122-3 | 40 | 47.3% Castor oil, 47.3% Akoline MCM, 5.4% benzyl alcohol + cholesterol (40 mg/g) | Solution to oil | Unchanged after 24 hours * | Starts to precipitate | |
| 42 | ACA09 1120-2 | 40 | 50% Castor oil, 50% Akoline MCM + cholesterol (60 mg/g) | Solution to oil | Very slight precipitation of crystal sin the entire sample after 24 h | | |
| 43 | ACA09 1108-3 | 45 | 45% Castor oil, 55% Akoline MCM + cholesterol (45 mg/g) | Solution to oil | Slight precipitation of crystals on the bottom after 9 days | | Crystals on the bottom after 1 week refrigerated |
| 44 | ACA09 1121-1 | 45 | 50% Castor oil, 50% Akoline MCM + cholesterol (67.5 mg/g) | Solution to oil | Slight precipitation of crystal sin the entire sample after 24 h | | |
| 45 | ACA09 1121-2 | 50 | 50% Castor oil, 50% Akoline MCM + cholesterol (75 mg/g) | Solution to oil | Very slight precipitations of crystal sin the entire sample after 24 h | | |
| 46 | ACA09 1216-2 | 5 | Olive oil | Emulsion to oil | Unchanged after 4 days, first signs of precipitation after 5 days | Crystals at the bottom after 9 months | |
| 47 | ACA09 1216-1 | 5 | Olive oil + cholesterol (10 mg/g) | Emulsion to oil | Unchanged after 3 weeks * | Unchanged after 8 months | |
| 48 | ACA09 1221-2 | 7.5 | Olive oil | Emulsion to oil | Precipitation after approx. 1 hour | | |
| 49 | ACA09 1221-1 | 7.5 | Olive oil + cholesterol (7.5 mg/g) | Emulsion to oil | Unchanged after 1 day, very slight precipitation after 1 week | Crystals at the bottom after 8 months | |

Examples 50-75

Examples 50 to 75 were carried out essentially as examples 1-49. Akoline Medium-Chain Monoglyceride (MCM) (Batch 8192270 and 8218940) and Akomed R Medium-Chain Triglyceride (MCT) (Batch 4765) were obtained from AarhusKarlshamns Sweden AB, Karlshamn, Sweden. Absolute ethanol (>99%) was obtained from VWR International.

The procedure for making and evaluating lipid-based formulations was as follows: The batch sizes were either 20 g or 100 g of final formulation. The desired amounts of 3-beta-hydroxy-5-alpha-pregnan-20-one and cholesterol were weighed in a round-bottomed flask, 250 or 1000 ml depending on the batch size.

To every gram of 3-beta-hydroxy-5-alpha-pregnan-20-one and cholesterol mixture a volume of about 15 to 30 ml of absolute ethanol was added. The smaller volume of alcohol per gram of solute was used when preparing the largest batch size of 100 g of final formulation. The mixture was treated in an ultrasonication bath (not exceeding 55° C.) until a clear solution was obtained. This was normally accomplished within a few minutes. The glycerides were then added and the resulting mixture was treated in the ultrasonication bath for a few seconds until a clear, homogeneous liquid was obtained. The alcohol was evaporated from the liquid on a rotary evaporator at a pressure of about 20 mbar and a temperature of about 40° C. until weight of the flask was more or less constant. Normally, the remaining ethanol content was 0.5% (w/w) or less. The evaporation time was 0.5-1.5 h, depending on the batch size. The aim was to obtain a practically uncolored liquid with the appearance of a clear oil at room temperature. The liquid was transferred to clear glass vials, which were stored at room temperature until evaluation.

Some selected formulations were portioned and stored at 2-8° C. for limited period of time.

The evaluation comprised observation of the physical stability at room temperature over time. The samples were observed for haziness, precipitation of particles, aggregates or crystals, and subsequent sedimentation and/or phase separation into two or more liquid phases, and/or change of colour.

It was possible to dissolve up to 25 mg of 3-beta-hydroxy-5-alpha-pregnan-20-one per gram of final formulation based on 50% MCT and 50% MCM (examples 68 and 69) without any noticeable change in appearance when stored at room temperature for more than 1 month. One of the samples (example 69) also withstood storage at 2-8° C. and repeated temperature cycling.

In order to check the robustness and reproducibility of the formulations and the procedure for the preparation thereof, a scaling up of the batch size from 20 g to 100 g of final formulation was performed. The compositions corresponding to examples 60 and 69 were selected for this procedure. From the behavior during preparation and the initial observations of the resulting formulations (examples 74 and 75) it can be concluded that the adopted procedure is both robust and reproducible for making up to 100 g of formulation.

TABLE 2

| Example | Batch name | Amount of UC1010 (mg/g) | Vehicle | Appearance at preparation | Appearance after 1-2 days at room temperature | Appearance after about 1 month (if not otherwise stated) at room temperature | Comments |
|---|---|---|---|---|---|---|---|
| 50 | ACA10 0129-1 | 30 | 50% Akoline MCM, 50% Akomed R MCT + cholesterol (30 mg/g) | Solution to oil | Signs of precipitation after 1 day | Precipitation | |
| 51 | ACA10 0129-2 | 30 | 50% Akoline MCM, 50% Akomed R MCT + cholesterol (45 mg/g) | Solution to oil | Signs of precipitation after 1 day | Precipitation | |
| 52 | ACA10 0129-3 | 28 | 50% Akoline MCM, 50% Akomed R MCT + cholesterol (56 mg/g) | Solution to oil | Unchanged | Precipitation | Signs of precipitation after 1 day in the refrigerator, substantial precipitation after 2 days |
| 53 | ACA10 0130-1 | 30 | 67% Akoline MCM, 33% Akomed R MCT + cholesterol (30 mg/g) | Solution to oil | Signs of slight precipitation after 2 days | Precipitation | |
| 54 | ACA10 0130-2 | 30 | 67% Akoline MCM, 33% Akomed R MCT + cholesterol (45 mg/g) | Solution to oil | Unchanged | Precipitation | |
| 55 | ACA10 0130-3 | 30 | 67% Akoline MCM, 33% Akomed R MCT + cholesterol (60 mg/g) | Solution to oil | Unchanged | Precipitation | |
| 56 | ACA10 0203-B | 20 | 50% Akoline MCM, 50% Akomed R MCT + cholesterol (40 mg/g) | Solution to oil | Unchanged | Unchanged after 29 weeks | Withstand 3 days in the refrigerator, but not 4 days, due to solidification of MCM |
| 57 | ACA10 0203-C | 20 | 50% Akoline MCM, 50% Akomed R MCT + cholesterol (60 mg/g) | Solution to oil | Unchanged | Unchanged after 29 weeks | Withstand 3 weeks in the refrigerator |
| 58 | ACA10 0204-1 | 20 | 50% Akoline MCM, 50% Akomed R MCT + cholesterol (100 mg/g) | Solution to oil | First signs of precipitation after a few hours, large star-shaped crystals after 2 days | Precipitation | |
| 59 | ACA10 0204-2 | 20 | 30% Akoline MCM, 70% Akomed R MCT + cholesterol (40 mg/g) | Solution to oil | Unchanged after 3 days | Precipitation | |
| 60 | ACA10 0206-1 | 20 | 30% Akoline MCM, 70% Akomed R | Solution to oil | Unchanged | Unchanged after 7 weeks | Withstand 6 days in the refrigerator, |

TABLE 2-continued

| Example | Batch name | Amount of UC1010 (mg/g) | Vehicle | Appearance at preparation | Appearance after 1-2 days at room temperature | Appearance after about 1 month (if not otherwise stated) at room temperature | Comments |
|---|---|---|---|---|---|---|---|
| | | | MCT + cholesterol (60 mg/g) | | | | but had precipitated after about 2 weeks without concomitant solidification of MCM Massive precipitation after 28 weeks |
| 61 | ACA10 0206-2 | 20 | 30% Akoline MCM, 70% Akomed R MCT + cholesterol (100 mg/g) | Solution to oil | First signs of precipitation after about 30 min | Precipitation | |
| 62 | ACA10 0206-3 | 20 | 15% Akoline MCM, 85% Akomed R MCT + cholesterol (40 mg/g) | Solution to oil | Precipitation | Precipitation | |
| 63 | ACA10 0206-4 | 20 | 15% Akoline MCM, 85% Akomed R MCT + cholesterol (60 mg/g) | Solution to oil | Unchanged after 1 days | Precipitation | |
| 64 | ACA10 0206-5 | 20 | 15% Akoline MCM, 85% Akomed R MCT + cholesterol (100 mg/g) | Solution to oil | Signs of precipitation directly after evaporation | Precipitation | |
| 65 | ACA10 0213-A | 20 | 100% Akomed R MCT + cholesterol (40 mg/g) | Solution to oil | Precipitation at the bottom | Precipitation | |
| 66 | ACA10 0213-C | 20 | 100% Akomed R MCT + cholesterol (60 mg/g) | Solution to oil | Precipitation in the whole sample | Precipitation in the whole sample | |
| 67 | ACA10 0213-B | 20 | 100% Akomed R MCT + cholesterol (80 mg/g) | Solution to oil | Precipitation directly after evaporation | Precipitation in the whole sample | |
| 68 | ACA10 0301-1 | 25 | 50% Akoline MCM, 50% Akomed R MCT + cholesterol (50 mg/g) | Solution to oil | Unchanged | Unchanged | A portion of the sample was placed in the refrigerator: partial solidification after 1 day, but clear solution after melting at RT. After another 1 day in the fridge the sample started to precipitate Massive precipitation after 25 weeks |
| 69 | ACA10 0301-2 | 25 | 50% Akoline MCM, 50% Akomed R MCT + cholesterol (75 mg/g) | Solution to oil | Unchanged | Unchanged after 25 weeks | A portion of the sample was placed in the refrigerator: partial solidification, |

TABLE 2-continued

| Example | Batch name | Amount of UC1010 (mg/g) | Vehicle | Appearance at preparation | Appearance after 1-2 days at room temperature | Appearance after about 1 month (if not otherwise stated) at room temperature | Comments |
|---|---|---|---|---|---|---|---|
| | | | | | | | but clear solution after melting at RT. The sample withstood repeated cycles during several weeks without precipitation! |
| 70 | ACA10 0301-3 | 25 | 50% Akoline MCM, 50% Akomed R MCT + cholesterol (100 mg/g) | Solution to oil | Very small amount of needle-shaped crystals after 1 day | Precipitation | A portion of the sample was placed in the refrigerator: partial solidification and very slight precipitation after melting at RT |
| 71 | ACA10 0301-4 | 30 | 50% Akoline MCM, 50% Akomed R MCT + cholesterol (60 mg/g) | Solution to oil | Unchanged after 3 days, slight tendency to precipitation after 5 days | Precipitation | A portion of the sample was placed in the refrigerator: partial solidification and slight precipitation after melting at RT |
| 72 | ACA10 0301-5 | 30 | 50% Akoline MCM, 50% Akomed R MCT + cholesterol (90 mg/g) | Solution to oil | Unchanged after 3 days, precipitation after 5 days | Precipitation | A portion of the sample was placed in the refrigerator: partial solidification and substantial precipitation after melting at RT |
| 73 | ACA10 0301-6 | 30 | 50% Akoline MCM, 50% Akomed R MCT + cholesterol (120 mg/g) | Solution to crystals (precipitated during evaporation; discarded) | — | — | — |
| 74 | ACA10 0320 | 25 | 50% Akoline MCM, 50% Akomed R MCT + cholesterol (75 mg/g) | Solution to oil | Unchanged | Unchanged | Batch size 100 g Very slight precipitation after 23 weeks |
| 75 | ACA10 0321 | 20 | 30% Akoline MCM, 70% Akomed R MCT + cholesterol (60 mg/g) | Solution to oil | Unchanged | Unchanged | Batch size 100 g Slight precipitation after 23 weeks |

Example 76

The objective of the study was to investigate the comparative pharmacokinetics in plasma of a 3-beta-hydroxy-5-alpha-pregnan-20-one formulation comprising sesame oil and cholesterol following subcutaneous administration to New Zealand White rabbits. Two groups of three female rabbits each received single doses 1 mg/kg (formulation as in example 7) or 5 mg/kg (formulation as in example 10).

Figure 1:
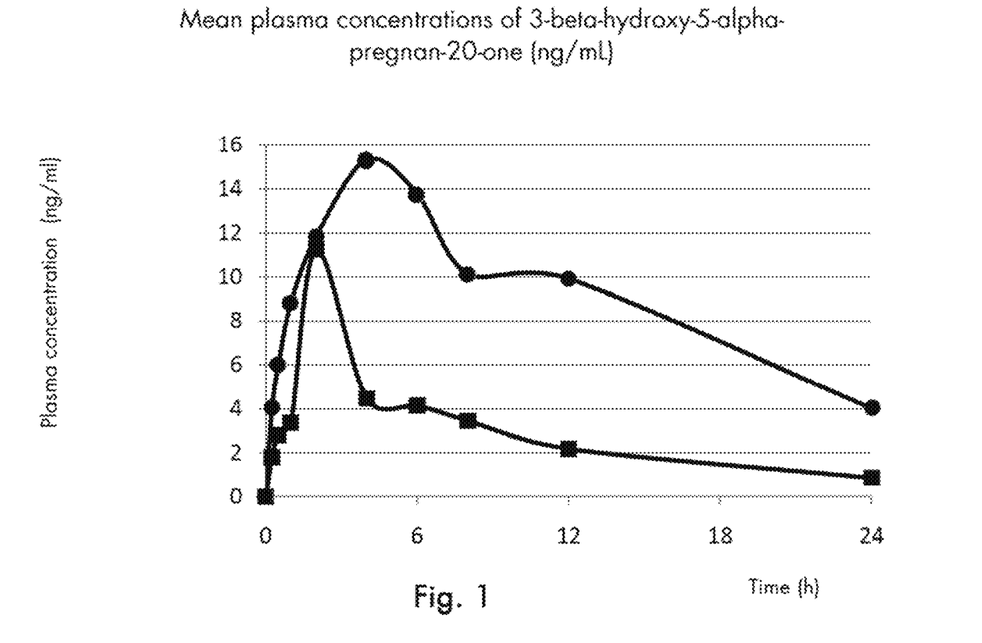
FIG. 1 shows mean plasma concentrations of 3-beta-hydroxy-5-alpha-pregnan-20-one (ng/mL) in rabbits following subcutaneous administration of 3-beta-hydroxy-5-alpha-pregnan-20-one in sesame oil with cholesterol (1:1) in two doses: 1 mg/kg (squares) and 5 mg/kg (circles).

Following subcutaneous injection into the dorsal neck region of the animals, blood samples were taken at 0.25, 0.5, 1, 2, 4, 6, 8, 12 and 24 hours post dose. Concentrations of 3-beta-hydroxy-5-alpha-pregnan-20-one in plasma were measured by a validated LC-MS/MS method. Data are presented in FIG. 1, and show mean plasma concentration (ng/mL) of 3-beta-hydroxy-5-alpha-pregnan-20-one for the two doses: 1 mg/kg (squares) and 5 mg/kg (circles).

Example 77

Figure 2:
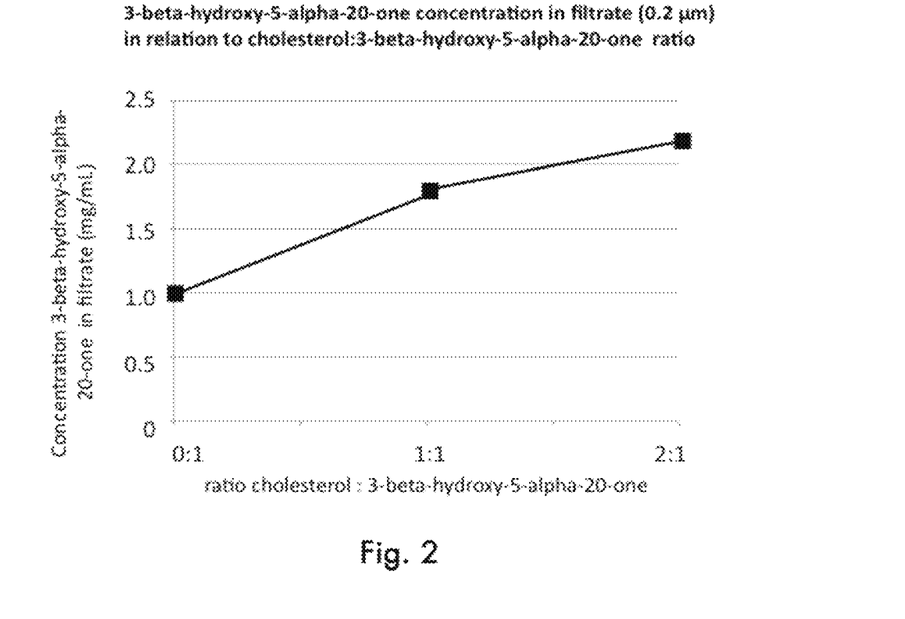
FIG. 2 shows 3-beta-hydroxy-5-alpha-pregnan-20-one concentration in filtrate (0.2 μm) from a suspension of 3-beta-hydroxy-5-alpha-pregnan-20-one in relation to cholesterol:3-beta-hydroxy-5-alpha-pregnan-20-one ratio.
Figure 3A:
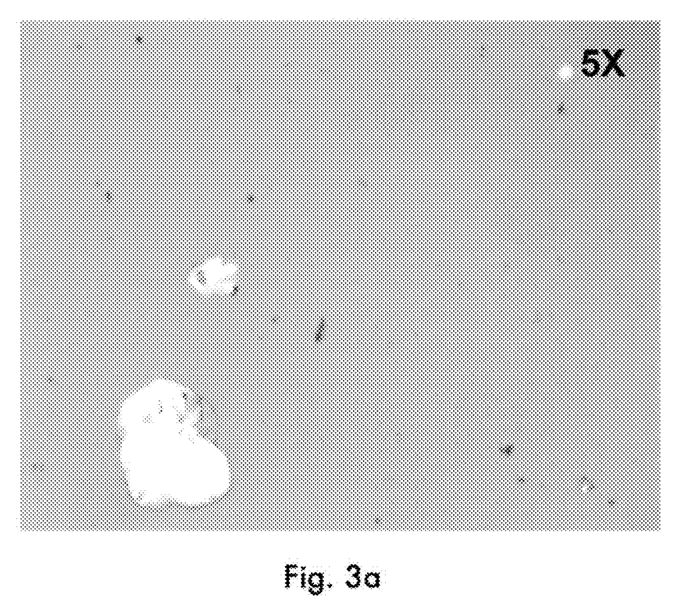
FIGS. 3a, 3b, 4a and 4b show photographs of suspensions of 3-beta-hydroxy-5-alpha-pregnan-20-one.
Figure 3B:
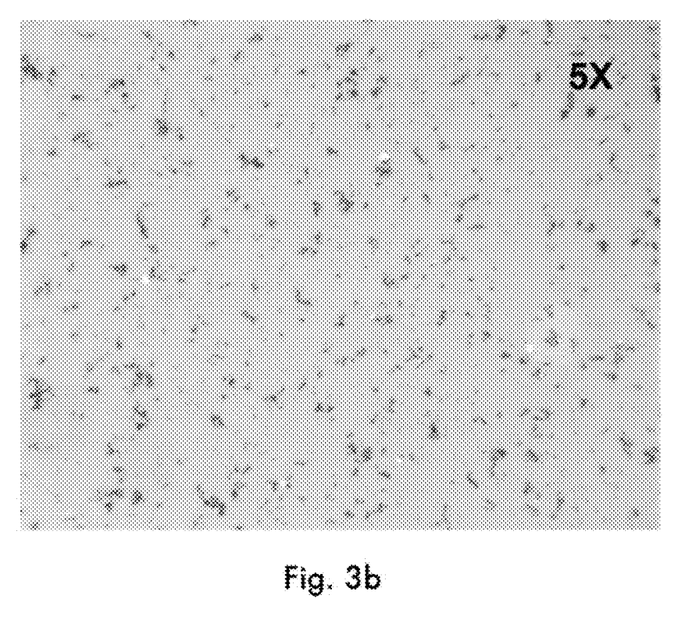

Suspensions of 3-beta-hydroxy-5-alpha-pregnan-20-one were prepared for investigation of solubility as follows: cholesterol was first dissolved at room temperature in sesame oil at 10 and 20 mg/ml, respectively. Suspensions of 3-beta-hydroxy-5-alpha-pregnan-20-one in sesame oil with different amounts of cholesterol were prepared on a magnetic stirrer at about 500 rpm using a conventional Teflon coated stir bar, at room temperature for several days, with occasional cycling to 2-8° C. At this time, the particles have become substantially smaller. Thereafter, samples of the respective suspensions were filtered through a 0.2 μm filter and analyzed with regard to concentration of 3-beta-hydroxy-5-alpha-pregnan-20-one. The results are presented in Table 3 and FIG. 2 where it can be seen that increasing the amounts of cholesterol increases the soluble fraction of 3-beta-hydroxy-5-alpha-pregnan-20-one. FIG. 2 shows data for a 3-beta-hydroxy-5-alpha-pregnan-20-one concentration of 10 mg/g. FIGS. 3*a* and 3*b* show microscopy pictures taken at 5× enlargement of suspensions with a 3-beta-hydroxy-5-alpha-pregnan-20-one concentration of 10 mg/g and a cholesterol:3-beta-hydroxy-5-alpha-pregnan-20-one ratio of 1:1 immediately upon mixing (3*a*) and after several days of stirring (3*b*).

TABLE 3

| The weight ratio cholesterol to 3-beta-hydroxy-5-alpha-pregnan-20-one | 3-beta-hydroxy-5-alpha-pregnan-20-one concentration in filtrate (mg/ml) | |
|---|---|---|
| | Initial 3-beta-hydroxy-5-alpha-pregnan-20-one concentration 10 mg/g | Initial 3-beta-hydroxy-5-alpha-pregnan-20-one concentration 40 mg/g |
| 0:1 | 1 | — |
| 1:4 | — | 1.4 |
| 1:2 | — | 1.9 |
| 1:1 | 1.8 | — |
| 2:1 | 2.2 | — |

Example 78

Figure 4A:
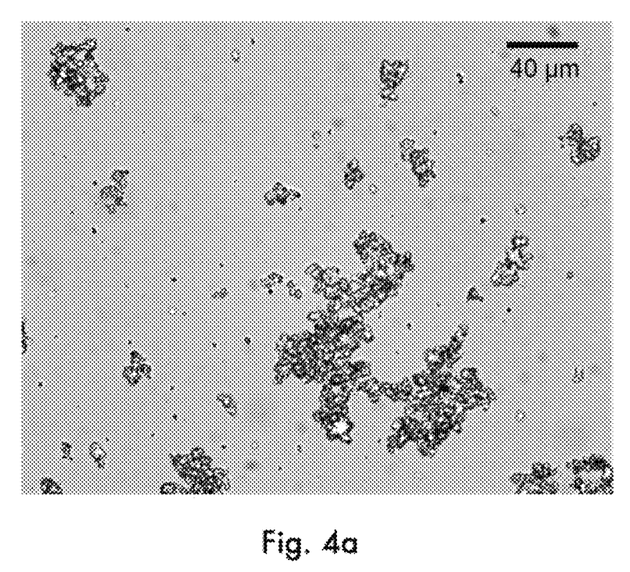
Figure 4B:
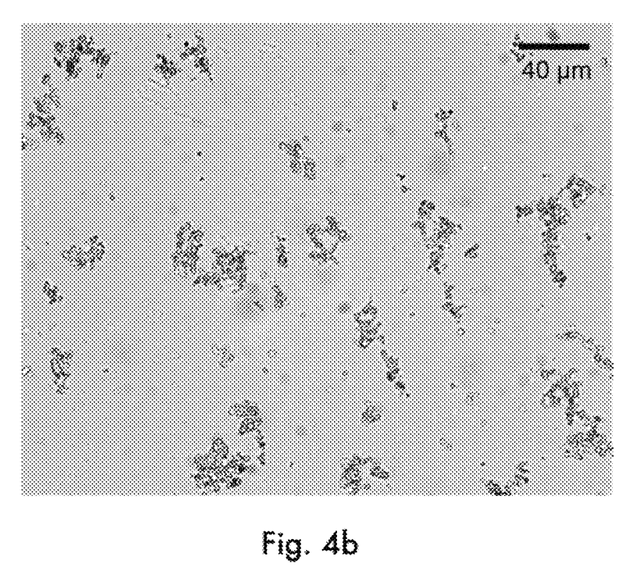

Micronized 3-beta-hydroxy-5-alpha-pregnan-20-one (10 mg/g) with a mean particle size of 6 micrometer was suspended in sesame oil with cholesterol (20 mg/g) and stirred as in example 77. Photos were taken immediately upon suspension (FIG. 4*a*) and after 19 hours of stirring (FIG. 4*b*).

CONCLUSION

It has been shown that the presence of a sterol such as cholesterol improves the possibilities to formulate 3-beta-hydroxy-5-alpha-pregnan-20-one in a pharmaceutical composition comprising acylglycerols, either as an oily solution or an oily suspension.

The invention claimed is:

1. A pharmaceutical composition, comprising:
   3-beta-hydroxy-5-alpha-pregnan-20-one;
   cholesterol; and
   a medium-chain triacylglycerol (MCT),
   wherein a weight ratio of said cholesterol to said 3-beta-hydroxy-5-alpha-pregnan-20-one is 1:5 to 2:1,
   wherein 3-beta-hydroxy-5-alpha-pregnan-20-one is present in an amount of up to 75 mg/g of the composition; and
   wherein at room temperature the composition is a liquid oil composition.

2. The pharmaceutical composition according to claim 1, wherein the MCT comprises a mixture of triacylglycerols which has a total combined percentage of (i) fatty acids with eight carbon atoms and (ii) fatty acids with ten carbon atoms of at least 95%.

3. The pharmaceutical composition according to claim 1, wherein the 3-beta-hydroxy-5-alpha-pregnan-20-one is suspended in a solution comprising the cholesterol and the MCT.

4. The pharmaceutical composition according to claim 1, wherein at least some of the 3-beta-hydroxy-5-alpha-pregnan-20-one is dissolved in a solution comprising the cholesterol and the MCT.

5. A pharmaceutical composition according to claim 1, wherein 3-beta-hydroxy-5-alpha-pregnan-20-one is present in an amount of up to 50 mg/g of the composition.

6. The pharmaceutical composition according to claim 1, wherein the composition further comprises a vegetable oil, and the vegetable oil is selected from the group consisting of sesame oil, peanut oil, olive oil, and castor oil.

7. The pharmaceutical composition according to claim 1, wherein said medium-chain triacylglycerol is a mixture of acylglycerols wherein the total combined percentage of fatty acids with 8 carbon atoms and 10 carbon atoms is at least 95%.

8. The pharmaceutical composition according to claim 1, wherein said medium-chain triacylglycerol comprises at least about 95% triacylglycerols.

9. The pharmaceutical composition according to claim 1, wherein said medium-chain triacylglycerol is a mixture of acylglycerols wherein the total combined percentage of fatty acids with 8 carbon atoms and 10 carbon atoms is at least 95% and said medium-chain triacylglycerol comprises at least about 95% triacylglycerols.

10. The pharmaceutical composition according to claim 1, wherein the weight ratio of said cholesterol to said 3-beta-hydroxy-5-alpha-pregnan-20-one is 1:4 to 2:1.

11. The pharmaceutical composition according to claim 1, wherein the weight ratio of said cholesterol to said 3-beta-hydroxy-5-alpha-prenan-20-one is 1:3 to 2:1.

12. The pharmaceutical composition according to claim 1, wherein said composition is formulated for parenteral administration.

13. The pharmaceutical composition according to claim 1, wherein the weight ratio of said cholesterol to said 3-beta-hydroxy-5-alpha-pregnan-20-one is 1:1 to 1:4.

14. The pharmaceutical composition according to claim 1, wherein the weight ratio of said cholesterol to said 3-beta-hydroxy-5-alpha-pregnan-20-one is 1:2 to 1:4.

15. The pharmaceutical composition according to claim 1, wherein the weight ratio of said cholesterol to said 3-beta-hydroxy-5-alpha-pregnan-20-one is 1:2.5 to 1.2:1.

16. The pharmaceutical composition according to claim 1, wherein the concentration of said cholesterol is no more than about 30 mg/ml.

17. The pharmaceutical composition according to claim 1, wherein 3-beta-hydroxy-5-alpha-pregnan-20-one is present in an amount of up to 40 mg/g of the composition.

18. The pharmaceutical composition according to claim 1, wherein 3-beta-hydroxy-5-alpha-pregnan-20-one is present in an amount of 25-40 mg/g of the composition.

19. A method of terminating steroid induced anesthesia, comprising: administering the pharmaceutical composition according to claim 1 to a subject in need thereof.

* * * * *